United States Patent
Kuo

(10) Patent No.: US 6,335,204 B1
(45) Date of Patent: Jan. 1, 2002

(54) FIXED VOLUME LIQUID TRANSFER DEVICE AND METHOD FOR TRANSFERRING LIQUIDS

(75) Inventor: Hai-Hang Kuo, Granger, IN (US)

(73) Assignee: Bayer Corporation, Elkhart, IN (US)

( * ) Notice: Subject to any disclaimer, the term of this patent is extended or adjusted under 35 U.S.C. 154(b) by 0 days.

(21) Appl. No.: 09/408,201

(22) Filed: Sep. 29, 1999

(51) Int. Cl.$^7$ ................................................. G01N 1/00
(52) U.S. Cl. ...................... 436/180; 422/100; 422/101; 422/922; 422/923; 73/863.32; 73/864.01; 436/174
(58) Field of Search ................. 422/100, 101, 422/93, 99, 922, 923; 73/863.32, 864.01; 436/174, 180

(56) References Cited

U.S. PATENT DOCUMENTS

| | | | |
|---|---|---|---|
| 2,097,571 A | * | 11/1937 | Moran |
| 4,037,464 A | * | 7/1977 | Wenanter |
| 4,057,499 A | * | 11/1977 | Buono |
| 4,197,735 A | * | 4/1980 | Munzer et al. |
| 4,483,825 A | * | 11/1984 | Fatchesw |
| 4,800,164 A | * | 1/1989 | Bisconte |
| 5,059,398 A | * | 10/1991 | Kenny |
| 5,456,885 A | * | 10/1995 | Coleman et al. |
| 5,460,782 A | * | 10/1995 | Coleman et al. |
| 5,770,158 A | * | 6/1998 | Eischen et al. ........................ |

* cited by examiner

*Primary Examiner*—Ana Fortuna
(74) *Attorney, Agent, or Firm*—Jerome L. Jeffers

(57) ABSTRACT

A fixed volume liquid transfer device defined by a small bore tube having an open end for collection of liquids and a plunger in the tube is disclosed. A piston is mounted around the open end and an air plug is mounted in the piston adjacent the open end. Liquid in a test tube is transferred to a testing site by inserting the transfer device into the test tube. As the piston contacts the liquid, the liquid is pumped into the tube. As the transfer device is inserted further, the air plug is actuated to balance air pressure across the piston. The device may then be withdrawn from the test tube and transported to a test site. At the test site, the plunger is depressed to expel the liquid into a testing device.

8 Claims, 3 Drawing Sheets

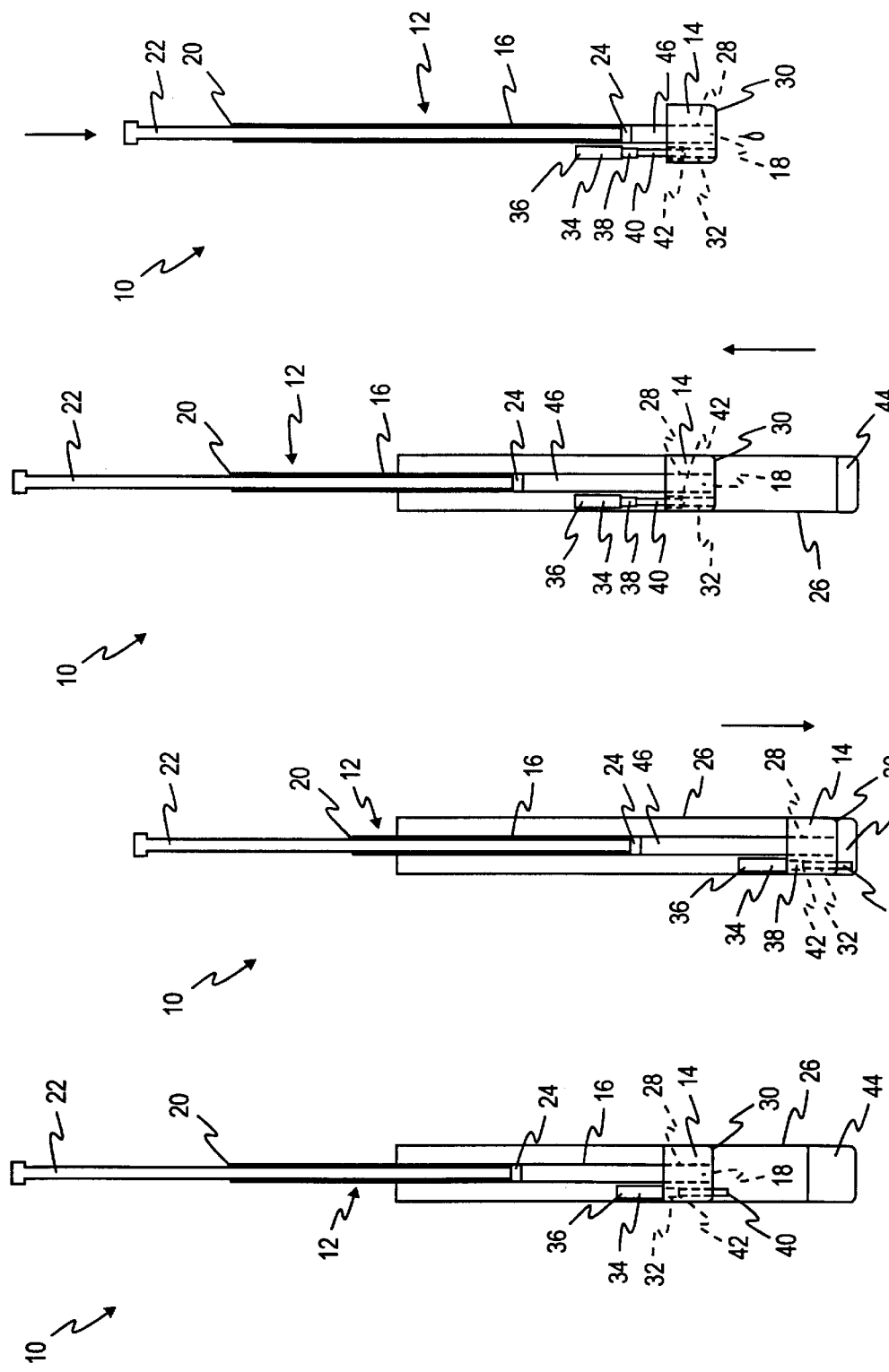

FIXED VOLUME LIQUID TRANSFER DEVICE AND METHOD FOR TRANSFERRING LIQUIDS

FIELD OF THE INVENTION

The present invention relates generally to a fixed volume liquid transfer device and to a method for transferring liquids and, more particularly, to a microdispenser with a piston for applying external pressure to liquid to fill the microdispenser in the process of transferring the liquid.

BACKGROUND OF THE INVENTION

Metering and transferring of reagents or samples are generally important in conducting diagnostic tests, especially those providing quantitative results. Apparatus or methods that can easily and quickly deliver accurate amounts of fluid or liquid are usually needed to achieve the desired assay performance. There are currently several products designed to serve this purpose. Among them, the Aqua-Cap™ microdispenser from Drummond Scientific Company of Broomall, Pa. is one of the devices suitable for point-of-care testing.

The Aqua-Cap™ microdispenser includes a plunger and a disposable glass capillary tube containing a porous plug located at a preset position. This product is a self-filling device that takes up liquid by capillary action. The liquid volume in the capillary is precisely controlled and maintained by the porous plug, which becomes impermeable to air when wetted. Following the filling process, the microdispenser functions exactly as a syringe in transporting and dispensing the liquid.

Although manual pipeting is not required in using prior art microdispensers such as the Aqua-Cap™ microdispenser, it is sometimes necessary to slant a tube containing a liquid to be transferred to facilitate the capillary filling. This assisting action, however, may not be acceptable in certain situations, particularly when the liquid is biohazardous. To avoid possible contamination caused by accidental spills in these cases, a liquid transfer device to take up a desired amount of liquid effectively without slanting the tube is desirable.

SUMMARY OF THE INVENTION

The present invention is a fixed volume liquid transfer device known as a microdispenser used for quantitative delivery of aqueous liquids or fluids in specimen collection, diagnostic testing, environmental monitoring, or other analytical measurements that require simple and rapid liquid transfer in their procedures.

The fixed volume liquid transfer device consists of a microdispenser defined by a tube having a plunger extending into the tube to dispense collected liquid. A porous plug or other volume control device is mounted in the microdispenser at a preset position below the plunger. The plug is formed of a material that becomes impermeable to air when it becomes wet upon contact by the collected liquid. The tube has an open end for the collection of liquids.

The fixed volume liquid transfer device also includes a piston. The piston has a centric hole into which extends the open end of the tube. The piston also includes an eccentric hole. An air plug is mounted in the eccentric hole and has a tip that extends out of the eccentric hole beyond the piston. In a first, static position, the air plug blocks passage of air through the eccentric hole. In a second position of the air plug the eccentric hole is open allowing the passage of air.

To transfer liquid, the microdispenser is inserted open end first into a test tube containing the liquid. The diameter of the piston is approximately the same as that of the test tube. The microdispenser is pushed down into the test tube. Once the piston contacts the liquid and insertion continues, a pumping action occurs which pumps or forces the liquid into the microdispenser through the open end. Air in the tube above the liquid escapes through the porous plug and around the plunger. Thus, capillary migration of liquid relied upon by prior art microdispensers is not used as the driving force in this filling process.

The tube fills with liquid until the liquid contacts the porous plug, wetting the plug and stopping the flow of liquid into the microdispenser tube. As the piston engages the bottom of the test tube, the tip of the air plug also engages the bottom of the test tube moving the air plug to its second position. In the second position of the air plug the eccentric hole in the piston is open and air on both sides of the piston is balanced. The microdispenser is then withdrawn from the test tube and, due to the open eccentric hole in the piston, air pressure across the piston is balanced and a vacuum below the piston is avoided. Thus, backflow of liquid in the microdispenser tube into the test tube is prevented.

The microdispenser is then transported to a test site and the plunger is depressed to dispense the collected liquid into a testing device.

BRIEF DESCRIPTION OF THE DRAWINGS

Other objects and advantages of the invention will become apparent upon reading the following detailed description and upon reference to the drawings in which:

FIG. 4 is a schematic view of the liquid transfer device positioned in a container of liquid to be transferred;

FIG. 5 is a view similar to FIG. 4 with the liquid transfer device in a liquid collecting position;

FIG. 6 is a view similar to FIGS. 4 and 5 during withdrawal of the liquid collection device from the container; and FIG. 7 is a schematic view of the liquid transfer device while it is dispensing the collected liquid.

DETAILED DESCRIPTION OF ILLUSTRATIVE EMBODIMENTS

Figure 1:
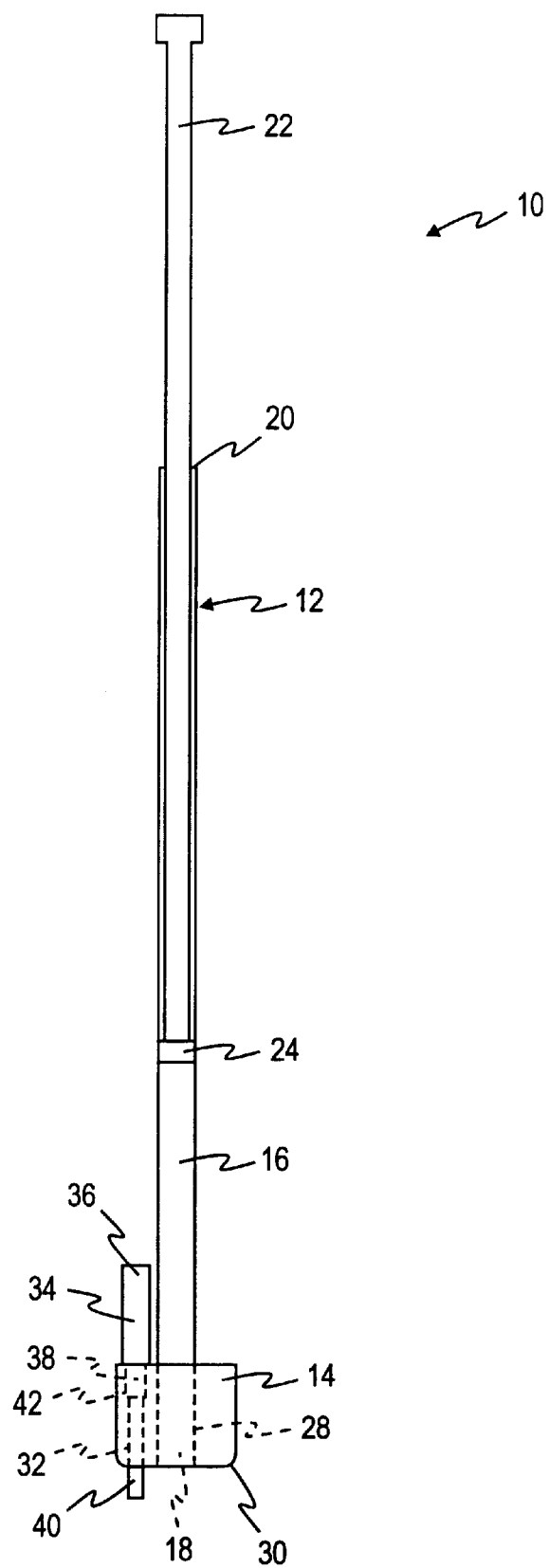
FIG. 1 is a partial cross sectional view of a fixed volume liquid transfer device constructed in accordance with the principles of the present invention.

Referring initially to FIG. 1, there is illustrated a fixed volume liquid transfer device 10 used for metering and transferring reagents or other fluids or liquids. The liquid transfer device 10 is defined by three components, a microdispenser 12, a piston 14, and an air plug 34. The microdispenser 12 is of the type disclosed in U.S. Pat. No. 5,059,398. The microdispenser 12 includes a disposable glass capillary tube or transfer tube 16 with a first open collection and dispensing end 18 and a second open end 20 that vents air in the tube 16. A plunger 22 is positioned in the tube 16 for dispensing collected fluid or liquid by pushing a porous plug 24 toward the first open end 18. The porous plug 24 is of a material such as polyethylene or other plastic material which has hydrophobic characteristics. Such material is available from Porex Technologies of Fairburn, Ga.

The plug 24 becomes impermeable to air when wetted by the collected liquid and is at a preset position in the tube 16 corresponding to the volume of liquid desired to be collected. When not wetted, the plug 24 freely passes air that flows along the plunger 22 and out of the second open end 20.

Figure 3:
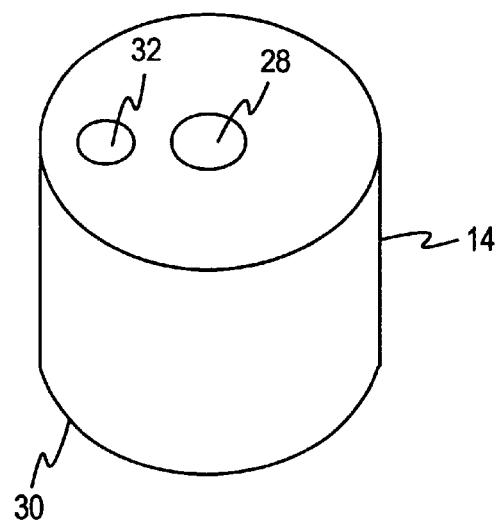
FIG. 3 is an enlarged view of a piston used with the liquid transfer device of FIG. 1.

The microdispenser 12 is a self-filling device that takes up liquid by capillary action. It is sometimes necessary in prior art microdispensers, however, to facilitate the capillary filling by slanting the test tube containing the liquid to be collected. This assisting action may not be acceptable when the liquid is biohazardous. To avoid possible contaminations caused by accidental spills, the liquid transfer device 10 uses a pumping action for liquid filling. The pumping action is provided by the piston 14. As best seen in FIG. 3, the piston 14 is a disk of elasomeric or similar material of a diameter and configuration approximately the same size as a container of liquid that is to be collected such as test tube 26 in FIGS. 4–7. The piston 14 includes a centric hole 28 extending through the piston 14. The first open end 18 of the transfer tube 16 is inserted into the centric hole 28 until it is adjacent a lower side 30 of the piston 14. The piston 14 also includes an eccentric hole 32. An air plug 34 is positioned in the eccentric hole 32.

Figure 2:
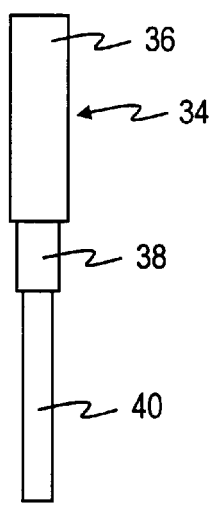
FIG. 2 is an enlarged view of an air plug used in the liquid transfer device of FIG. 1.

As best seen in FIG. 2, the air plug 34 includes a head 36, a shoulder 38 and a tip 40. The eccentric hole 32 is stepped such that in a closed position of air plug 34, the shoulder 38 engages a step 42 in the eccentric hole 32 and blocks the flow of air. In this closed position, the tip 40 of the air plug 34 extends out of the eccentric hole 32 beyond the lower side 30 of piston 14 (FIGS. 1, 4 and 5). There is also an open position of the air plug 34. In this open position, the air plug 34 is moved up and the shoulder 38 does not engage the step 42 (FIGS. 6 and 7). In the open position of the air plug 34, air can pass through the eccentric hole 32 balancing air pressure across the piston 14.

The operation of the fixed volume liquid transfer device 10 and the method of transferring liquids are illustrated in FIGS. 4–7. A liquid 44 contained in the test tube 26 is to be collected and transferred using the liquid transfer device 10. To collect the liquid 44, the liquid transfer device 10 with the air plug 34 in the closed position is inserted into the test tube 26 (FIG. 4). As the device 10 is inserted into the test tube 26, air in the test tube 26 passes up the transfer tube 16, through the plug 24 and out of the second open end 20. Once the lower side 30 of the piston 14 contacts the liquid 44, external pressure is applied to the liquid 44 causing a pumping action that pumps the liquid 44 into the transfer tube 16. Liquid fills the transfer tube 16 to the level defined by the plug 24. Once the plug 24 is wetted, air cannot pass through it and no further filling of the transfer tube 16 occurs. As this occurs, the tip 40 of the air plug 34 engages the bottom of the test tube 26 moving the air plug 34 to the second or open position (FIG. 5). In the open position of the air plug 34, air is balanced across the piston 14 and prevents the backflow of the collected liquid 46 as the liquid transfer device 10 is withdrawn from the test tube 26 (FIG. 6).

The liquid transfer device 10 may then be moved to a test site or test device and the collected liquid 46 is dispensed by pressing the plunger 22 and the plug 24 down the transfer tube 16 toward the first open end 18. Once the liquid is dispensed, the liquid transfer device 10 can be disposed of in the appropriate manner.

While the present invention is susceptible to various modifications and alternative forms, a specific embodiment has been shown by way of example in the drawings and will be described in detail. It should be understood, however, that it is not intended to limit the invention to the particular forms disclosed, but on the contrary, the intention is to cover all modifications, equivalents, and alternatives falling within the scope and spirit of the invention, as defined by the appended claims:

What is claimed is:

1. A liquid transfer device, comprising:

a small bore tube having a first open end for collection of liquids, a piston mounted on said tube adjacent said first open end, and air plug mounted in said piston, a porous plug that is impermeable to air when wetted, said plug mounted in said tube and spaced from said first open end at a distance defining a predetermined volume of liquid to be transferred, and a plunger mounted in said small bore tube.

2. The liquid transfer device claimed in claim 1 wherein said piston includes a centric hole and an eccentric hole, said tube being located in said centric hole.

3. The liquid transfer device claimed in claim 1 wherein said piston includes a centric hole and an eccentric hole, an air plug mounted in said eccentric hole, said air plug including a tip extending out of said eccentric hole.

4. A microdispenser, comprising:

a tubular body including a first open end for the introduction of fluid into said tubular body, a piston having a first hole, said tubular body mounted in said first hole with said piston adjacent said first open end and at least partially encircling said tubular body, wherein said piston includes a second hole, an air release device moveable in said second hole, said air release device including a tip extending out of said second hole;

a porous plug mounted in said tubular body, and a plunger in said tubular body.

5. In a fixed volume liquid transfer device of the type including a tubular body with a first open end through which fluid flows into said tubular body, and a fluid volume control device in said tubular body at a preselected position, the improvement comprising:

a piston mounted on an encircling said tubular body adjacent said first open end, and air plug mounted in said piston adjacent said open end, said air plug moveable relative to said piston, wherein said piston includes a centric hole and an acentric hole, said tubular body being in said centric hole, and said air plug mounted in said acentric hole.

6. A method of transferring fluids from a test tube using a micropipette having a tubular body, said tubular body having an open end for receiving fluids, a plunger in said tubular body and a device for controlling the volume of fluid introduced into said tubular body, comprising:

mounting a piston on said tubular body adjacent the open end of said tubular body, said piston dimensioned and configured substantially the same as the inside configuration of a test tube, applying external pressure on said fluid in said test tube by inserting said micropipette with said piston into said text tube containing fluid to be transferred until said piston engages a bottom of said test tube, collecting fluid in said tubular body, wherein said piston is further provided with an air plug, said air plug having an open and closed positions; and engaging said air plug with said test tube to actuate said air plug to said open position and valance air pressure across said piston.

7. The method of transferring fluids claimed in claim 6 further comprising, pulling said micropipette with said piston out of said test tube.

8. The method of transferring fluids claimed in claim 7 further comprising, pushing said plunger into said tubular body to dispense the collected fluid out of said tubular body.

* * * * *